US005681816A

United States Patent [19]

Korman

[11] Patent Number: 5,681,816
[45] Date of Patent: Oct. 28, 1997

[54] METHOD OF INDUCING TEMPORARY PARALYSIS OF THE GASTROINTESTINAL TRACT DURING MEDICAL PROCEDURE

[76] Inventor: Louis Y. Korman, 11424 Cushman Rd., Rockville, Md. 20852

[21] Appl. No.: 122,468

[22] PCT Filed: Apr. 24, 1992

[86] PCT No.: PCT/US92/03369

§ 371 Date: Feb. 22, 1994

§ 102(e) Date: Feb. 22, 1994

[87] PCT Pub. No.: WO92/19261

PCT Pub. Date: Nov. 12, 1992

[51] Int. Cl.[6] ............................................. A61K 38/00
[52] U.S. Cl. ............................................................ 514/12
[58] Field of Search .................................................. 514/12

[56] References Cited

U.S. PATENT DOCUMENTS

| | | | |
|---|---|---|---|
| 3,880,826 | 4/1975 | Said et al. | 260/112.5 |
| 4,370,317 | 1/1983 | Jorgensen et al. | 424/177 |
| 4,598,065 | 7/1986 | Lundt et al. | 514/12 |
| 4,605,641 | 8/1986 | Bolin et al. | 514/12 |
| 4,734,400 | 3/1988 | Bolin et al. | 514/12 |
| 4,822,774 | 4/1989 | Ito et al. | 514/12 |
| 4,835,252 | 5/1989 | Musso et al. | 530/324 |
| 4,939,224 | 7/1990 | Musso et al. | 530/324 |
| 5,055,302 | 10/1991 | Laties et al. | 530/324 |

OTHER PUBLICATIONS

The Merck Index, 10th Ed. Windholz et al. N.J. (1983) pp. 434–434, Abstract No. 2967.
Ross, W., "Premedication for Upper Gastrointestinal Endoscopy," *Gastrointestinal Endoscopy* 35(2):120 (1989).
Goodman and Gilman, In: *The Pharmalogical Basis of Therapeutics*, 5th Ed., MacMillan (ed.), New York, pp. 514–532 (1975).
Norfleet, R.G., "Premedication for Colonoscopy," *Gastrointestinal Endoscopy*, 24:164 (1978).
Gregerson, et al., "The Effects of Glucagon and Glucagon–(1–21)–Peptide on Androduodenal Motility in Healthy Volunteers," *Scand. J. Gastroenterol.*, 23 (Supp 152) :42 (1988).
Larsen, et al., "The Effect of Glucagon, Glucagon–(1–21)–Peptide, and Placebo on Duodenal Pressure Activity in Healthy Subjects," *Scand. J. Gastroenterol.*, 21:634 (1986).
Diamant et al., "Spasmolytic Action and Clinical User of Glucagon," in *Handbook Experimental Pharm*, Lefevre (ed.), 66 (2): 611 (1983).
Kreen, L., "Pharmacoradiology in Barium Examinations with Special Reference to Glucagon," *Br. J. Radiol.*, 48:691 (1975).
Said, S., V. Mutt, "Isolation from Porcine–Intestinal Wall of Vasoactive Octacosapeptide Related to Secretin and to Glucagon," *Eur. J. Biochem*, 28:199 (1972).
Said, S.I., V. Mutt, "Polypeptide with Broad Biological Activity: Isolation from Small Intestine," *Science*, 169:1217 (1970).
Bunnett, et al., "Isolation and Sequence Analysis of Vasoactive intestinal Peptide from a Ganglioneuroblastoma," *Clin. Endocrinol. Metab.*, 59:1133 (1984).
Khalil, et al., Vasoactive Intestinal Peptide, In: *Gastrointestinal Endocrinology*, J.C. Thompson (ed.), McGraw Hill, New York, pp. 260–272 (1987).
Grider and Makhlouf, "Colonic Peristaltic Reflex: Identification of Vasoactive Intestinal Peptide as Mediator of Descending Relaxation," *Amer. J. Physiol.*, 25:G40 (1986).
Maggi, et al., "Human Isolated Ileum: Motor Responses of the Circular Muscle to Electrical Field Stimulation and Exogenous Neuropeptides," *Naunyn–Schmiedeberg's Arch Pharmacol*, 341:256 (1990).
Grider, et al., Vasoactive Intestinal Peptide as a Neural Mediator of Gastric Relaxation, *Amer. J. Physiol.*, 248:G73–G78 (1985).
Grider, J., "Identification of Neurotransmitters Regulating Intestinal Peristaltic Reflex in Humans," *Gastroenterology*, 97:1414 (1989).
Burleigh, D.E., "Motor Responsiveness of Proximal and Distal Human Colonic Muscle Layers to Acetylcholine, Noradrenaline, and Vasoactive Intestinal Peptide," *Dig. Dis. Sci.*, 35(5):617 (1990).
Anuras, "Effects of Some Gastrointestinal Hormones on Two Muscle Layers of Duodenum," et al., *Amer. J. Physiol.*, 234:E60 (1978).
Cohen, and S. Landry, "Vasoactive Intestinal Polypeptide, Increased Tone, Enhancement of Acetylcholine Release, and Stimulation of Adenylate Cyclase in Intestinal Smooth Muscle," *Life Sciences*, 26:816 (1990).
Fontaine, et, al., "Evidence against VIP as the Inhibitory Transmitter in Non–adrenergic, Noncholinergic Nerves Supplying the Longitudinal Muscle of the Mouse Colon," *Br. J. Pharmac.*, 89:599 (1986).
Gordon, et al., "Vasoactive Intestinal Polypeptides Induce Guinea-Pig Ileum Contraction by Causing Release of Endogenous Acetylcholine," *Arch. Int. Pharmacodyn.*, 305:14 (1990).
Ellis, S.G., et al., "Present Status of Rescue Coronary Angioplasty; Current Polarization of Opinion and Randomized Trials," *J. Amer. Coll. Cardiol,*, 19:681 (1992).
Brook, R.H., et al., "Predicting the Appropriate Use of Carotid Endarterectomy, Upper Gastrointestinal Endoscopy, and Coronary Angiography," *New. Eng. J. Medicine*, 323:1173 (1990).
Rao, P.S., "Balloon Angioplasty of Aortic Coartation: A Review," *Clin. Cardiol.*, 12:618 (1989).

(List continued on next page.)

Primary Examiner—Kevin E. Weddington
Attorney, Agent, or Firm—Rae-Venter Law Group, P.C.

[57] ABSTRACT

A method of inducing a temporary substantial paralysis of an area of interest in a patient undergoing a medical procedure is provided. The method involves administering a therapeutically effective amount of vasoactive intestinal peptide (VIP) admixed with a pharmaceutically acceptable carrier to a patient undergoing an endoscopy or other medical procedure.

19 Claims, 9 Drawing Sheets

OTHER PUBLICATIONS

Manyari, D.E., et al., "Nuclear Cardiology Techniques in the Assessment of Ischemic Heart Disease," *Clin. Invest. Med.*, 9:76 (1986).

Kotler, T.S., et al., "Exercise Thallium–201 Scintigraphy in the Diagnosis and Prognosis of Coronary Artery Disease," *Ann. Intern. Med.*, 113:684 (1990).

Iskandrian, A.S., "Single–photon Emission Computed Tomographic Thallium Imaging with Adenosine, Dipyridamole, and Exercise," *Amer. Heart J.*, 122:279 (1991).

Bjorkhem, G., et al., "Myocardial Scintigraphy with 201–Thallium in Pediatric Cardiology: A review of 52 Cases," *Pediatr. Cardiol.*, 11:1 (1990).

Bitar, K.N., and G.M. Makhlouf, "Relaxation of Isolated Gastric Smooth Muscle Cells by Vasoactive Intestinal Peptide," Science, 216:351 (1982).

Grider, J.R., and J.R. Rivier, "Vasoactive Intestinal Peptide (VIP) as Transmitter of Inhibitory. Motor Neurons of the Gut: Evidence from the U VIP Antagonists and VIP Antiserum," *J. Pharmacol. Expt. Therapeutics*, 253(3):738 (1990).

Siegel et al., "Effects of Vasoactive Intestinal Peptide (VIP) on Lower Esophageal Sphincter in Awake Baboons," *Digest. Diseases Sci.*, 24(5):345 (1979).

Grider J.R., "Regulation of Intestinal Peristalsis by Neuropeptides," *Reg. Peptide Let.*, 1(4):1 (1989).

Biancani, P., and J. Behar, "Sphincters of the Gut: Regulation by Neuropeptides and Neurotransmitters," *Reg. Peptide Let.*, 1(4):6 (1989).

Qvigstad et al., "Comparison of Glucagon, Atropine, and Placebo as Premedication for Endoscopy of the Upper Gastrointestinal Tract," *Scand. J. Gastroent*, 14:231 (1979).

METHOD OF INDUCING TEMPORARY PARALYSIS OF THE GASTROINTESTINAL TRACT DURING MEDICAL PROCEDURE

This application is a 371 of PCT/US92/03369 filed Apr. 24, 1992.

The present invention relates to a method for inducing temporary paralysis of the gastrointestinal tract by administering vasoactive intestinal peptide (VIP) to a patient during the course of an endoscopy or other medical procedure.

BACKGROUND OF THE INVENTION

Gastrointestinal endoscopy is a diagnostic and therapeutic procedure which involves visual examination of different portions of the gastrointestinal tract using a long flexible tube known as an endoscope. An endoscope has a lens on one end and an eyepiece or video display system at the opposite end. Endoscopy is performed in moderately sedated patients by inserting the endoscope through the mouth or rectum and positioning the lens in the desired area of observation. Because the gastrointestinal tract is actively contracting during the procedure, the attending physician's visualization of certain regions of the GI tract is impaired or limited. In addition, this natural peristaltic reflex renders difficult the biopsy of certain areas of the GI tract and often interferes with the removal of polyps. In the case of attempted polyp removal, the procedure is made more difficult since the colon may be contracting when the polyps are being snared, cauterized and removed. The esophagus also moves at inopportune times such as when dilated veins known as vatices are being injected.

Attempts to reduce gastrointestinal contractions in endoscopic procedures have involved the use of several different agents over the years. In particular, atropine and glucagon have been employed as premedications for this purpose.

Atropine is a belladonna alkaloid with competitive antimuscarinic actions. In the gastrointestinal tract it is an inhibitor of oral secretion and gastrointestinal motility. However, it is known by practitioners in the field to be only marginally effective as a paralytic agent for use in endoscopic procedures. In fact, controlled studies have failed to demonstrate any beneficial effects of atropine during endoscopies with regard to improvement in patient tolerance or facilitation of endoscopy (Ross, W., Gastrointestinal Endoscopy, Vol.35, No 2, 120–126, 1989). Atropine is also associated with undesirable side effects such as blurred vision, headache, and urinary retention (Goodman and Gilman, The Pharmacological Basis of Therapeutics, 5th Ed., MacMillan, New York, 1975 pp. 514–532) and an increased risk of cardiac arrhymthias (Ross, W., Gastrointestinal Endoscopy, Vol. 35, No. 2, 120–126, 1989). Consequently, atropine is rarely used as a premeditation in endoscopy today.

Glucagon has been demonstrated to cause a variable reduction in gastroduodenal motility. The effect of glucagon appears to be dose-dependent with a minimally effective dose being 0.5 mg. However, glucagon does not facilitate colonoscopic evaluation (Norfleet, R. G., Gastrointestinal Endoscopy, Vol. 24, 164–5, 1978). In addition, it has been shown that even at doses as high as 2 mg, glucagon does not reduce contractions in the antrum (Gregerson et al., Scan. J. Gastroenterol. 23 (Supp 152) 42–47, 1988).

Glucagon administered intravenously at a dose of 1 mg followed by 2 mg IV over a period of 2 hours does affect, however, antroduodenal activity. That is, the cycle length and time between contractile activity in the duodenum is significantly increased while the mean pressure period is decreased (Larsen et al., Scand. J. Gastroenterol. Vol 21, 634–640, 1986).

Nausea and vomiting are two side effects associated with the use of glucagon. They are dose dependent, and can appear at a dose of 1 mg (Larsen et al., Scand. J. Gastroenterol. 21:634–640, 1986; Gregersen et al., Scand. J. Gastroent. 23 (Supp 152):42–47, 1988; Diamant Handbook Experimental Parm, Lefevre ed., Vol. 66/2:611–643, 1983). Since dosages required to sufficiently reduce motility frequently exceed 1 mg, side effects from glucagon use are prevalent. Such side effects render the patient extremely uncomfortable and often cause the endoscopic procedure to be interrupted or aborted.

Glucagon is used with a certain amount of success to facilitate barium examinations of the upper and lower GI tract by causing a dilation of the stomach and small bowel (Kreen, L., Br. J. Radiol., 48, 691–703, 1975). In addition, because of its effect on duodenal motility, glucagon has found use in endoscopic retrograde cholangiopancreatography (ERCP) to decrease contractions prior to cannulation of the ampulla of Vater.

Because of low efficacy and negative side effects, neither atropine nor glucagon have gained widespread use as gastrointestinal motility inhibitors. As a result, most upper and lower endoscopic examinations are performed without the benefit of halted peristalsis. Active peristalsis may prolong the procedure and leave the patient uncomfortable and the endoscopic procedure difficult and unpredictable. Thus the need for a safe, effective gastrointestinal paralytic agent with little or no side effects is great.

VIP is a 28 amino acid polypeptide hormone (Said, S., Mutt, V., Eur. J Biochem 28:199, 1972). It was first isolated in 1969 from normal hog lung and was shown at that time to cause a gradual but prolonged peripheral vasodilation. The polypeptide was given the name vasoactive intestinal peptide (VIP) in 1970 when it was isolated from porcine intestine (Said, SI, Mutt, V., Science 169:1217, 1970). Since then, it has been isolated and its amino acid sequence determined in rat, pig, cow, guinea pig and human. Interestingly, the amino acid sequence of VIP isolated from all sources is identical except in guinea pig, where it differs by four non-polar amino acid substitutions. The amino acid sequence of human VIP has been published (Bunnett et al., Clin. Endocrinol. Metab. 59:1133–1137; 1984), and is shown in Table 1.

TABLE 1

Amino Acid Sequence of VIP

| | |
|---|---|
| 1 | 10 |
| His—Ser—Asp—Ala—Val—Phe—Thr—Asp—Asn—Tyr— | |
| 11 | 20 |
| Thr—Arg—Leu—Arg—Lys—Gln—Met—Ala—Val—Lys— | |
| 21 | |
| Lys—Tyr—Leu—Asn—Ser—Ile—Leu—Asn—$NH_2$ | |

VIP immunoreactive neurons and nerve fibers have been found throughout the central nervous system and are widely distributed in many organ systems such as the genitourinary, gastrointestinal, respiratory, and cardiovascular systems (Khalil, et al., 'Vasoactive Intestinal Peptide' in *Gastrointestinal Endocrinology*, Ed. J. C. Thompson, McGraw Hill, New York (1987) pp 260–272. Gastrointestinal motility is responsible for the orderly movement of secretions and nutrients through discrete anatomic portions of the gastrointestinal tract. An extensive neural and hormonal system regulates this complex mixing and propulsive activity. Neurotransmitters released by gastrointestinal neurons and hormones found in the circulation and enterochromaffin cells are the chemical messengers responsible for coordinating gastrointestinal function.

The action of these messengers on target cells may be contradictory. The circuitry of the enteric nervous system is such that an agent may stimulate a target cell and at the same time stimulate the release of another agent that inhibits the target cell. Thus, the action of an agent on the intact-system cannot be predicted by the action on the individual cell. This has been found to be especially true when the data from various in vitro studies using isolated muscle strips exposed to different agents are compared to results seen in the clinical endoscopic setting.

For example, in rat and guinea pig isolated midcolon sections, atropine strongly inhibits ascending contractions at all grades of stretch but has no effect on descending relaxation (Grider and Makhlouf, Amer. J. Physiol. Soc. 25:G40–G45, 1986). Similarly, in isolated human ileum, atropine shows a primary relaxation in response to electrical field stimulation at all frequencies tested (Maggi et al., Naunyn-Schmiedebergts Arch Pharmacol. 341:256–261, 1990). As previously discussed, however, atropine offers minimal if any beneficial effects in reducing gastrointestinal motility in the endoscopic setting.

The action of VIP on in vitro gastrointestinal motility is dependant on the experimental model, species, location within the gastrointestinal tract, and muscle layer examined. Several in vitro animal studies have suggested that VIP is responsible for relaxation of rat stomach and colon, guinea-pig stomach and gallbladder, chick rectum and rectal cecum, and human intestine (Grider and Makhlouf, Am. J. Physiol., 25:G40–G45, 1986; Grider, et al., Am. J. Physicol., G73–G78, 1985; Grider, J., Gastroenterology, 97 1414–9, 1989; Said, et al., U.S. Pat. No. 3,880,826, 1975).

Several other studies in human, rabbit, guinea pig and mouse gastrointestinal tract suggest that VIP either has no effect or actually stimulates contractions in the gastrointestinal tract. For example, in distal human colon, VIP caused a small relaxation in circular muscle but did not relax longitudinal muscle contractions (Burleigh, D. E., Dig. Dis. Sci, Vol. 35, No. 5:617–621, 1990).

Additionally, in guinea pig and rabbit small intestine, oat duodenum, and mouse colon, VIP stimulated contractions of the layers of smooth muscle. In opossum duodenum, VIP stimulated contractions while glucagon stimulated relaxation (Anuras et al. Am. J. Physiol. 234:E60–E63, 1978; Cohen and Schwab Landry, Life Sciences, Vol. 26, 816–822, 1990;Fontaine, et. al., Br. J. Pharmac., 89:599–602, 1986; Said et al., U.S. Pat. No. 3,880,826, 1975;Gordon et al., Arch. int. Pharmacodyn. 305, 14–24, 1990).

SUMMARY OF THE INVENTION

The present invention provides a method for facilitating diagnostic and therapeutic endoscopic procedures by producing a short-lived paralysis of at least a portion of the gastrointestinal tract. The method involves administering to a patient during the course of an endoscopic procedure a therapeutically effective amount of vasoactive intestinal peptide (VIP) admixed with a pharmaceutically acceptable carrier.

Injection of VIP during gastrointestinal endoscopy results in a transient reduction in gastrointestinal motility. After injection of the appropriate dose of VIP into the blood stream, gastrointestinal contractions are halted almost immediately. The paralytic effect lasts about seven minutes. Additional amounts of VIP will extend the period of paralytic effect. The gastroparetic action of VIP occurs without a significant effect on blood pressure. VIP maybe used in a variety of circumstances in which cessation of gastrointestinal contraction results in significant clinical effect. A particular advantage of the method of the present invention is that it has been found that it is free of the negative side effects of nausea and vomiting associated with prior techniques.

By administering the proper dosage of VIP to a patient undergoing endoscopy, and therefore inducing a temporary paralysis of the gastrointestinal tract, a physician is better able to view the different anatomical portions of the gastrointestinal tract and therefore better able to offer a clinical diagnosis.

In addition, certain clinical procedures are facilitated. The paralytic effect on the gastrointestinal tract which VIP induces when administered during an endoscopy affords the physician greater precision in positioning medical instruments. Since peristaltic motion of the colon is abated, polyps are more easily removed. Because esophageal contractions are greatly reduced or eliminated, varices are more easily injected. During endoscopy, the injection of VIP also facilitates the examination and treatment of an arteriovenous malformation (AVM). In such procedure, the VIP is normally injected into the circulation as described above. It is also possible if preferred to inject the VIP in the vicinity of the AVM.

Another embodiment of the invention includes a method of dilating an intestinal blood vessel during the course of an abdominal anglographic procedure. Cannulation of the ampulla of Vater is greatly facilitated in endoscopic retrograde angiopancreatography (ERCP) since contractions in the duodenum are significantly reduced. In addition, VIP can be used in the course of vascular surgery to control arterial spasms.

Use of VIP during a barium exam relieves spasms in the bowel, thereby enabling the barium to better outline an area of the GI tract. This improves the attending physician's visibility under fluoroscopy and x-ray.

VIP may also be administered to a patient throughout the course of a cystoscopy to induce a temporary paralysis of the urinary tract.

DETAILED DESCRIPTION OF THE INVENTION

Figure 1A:
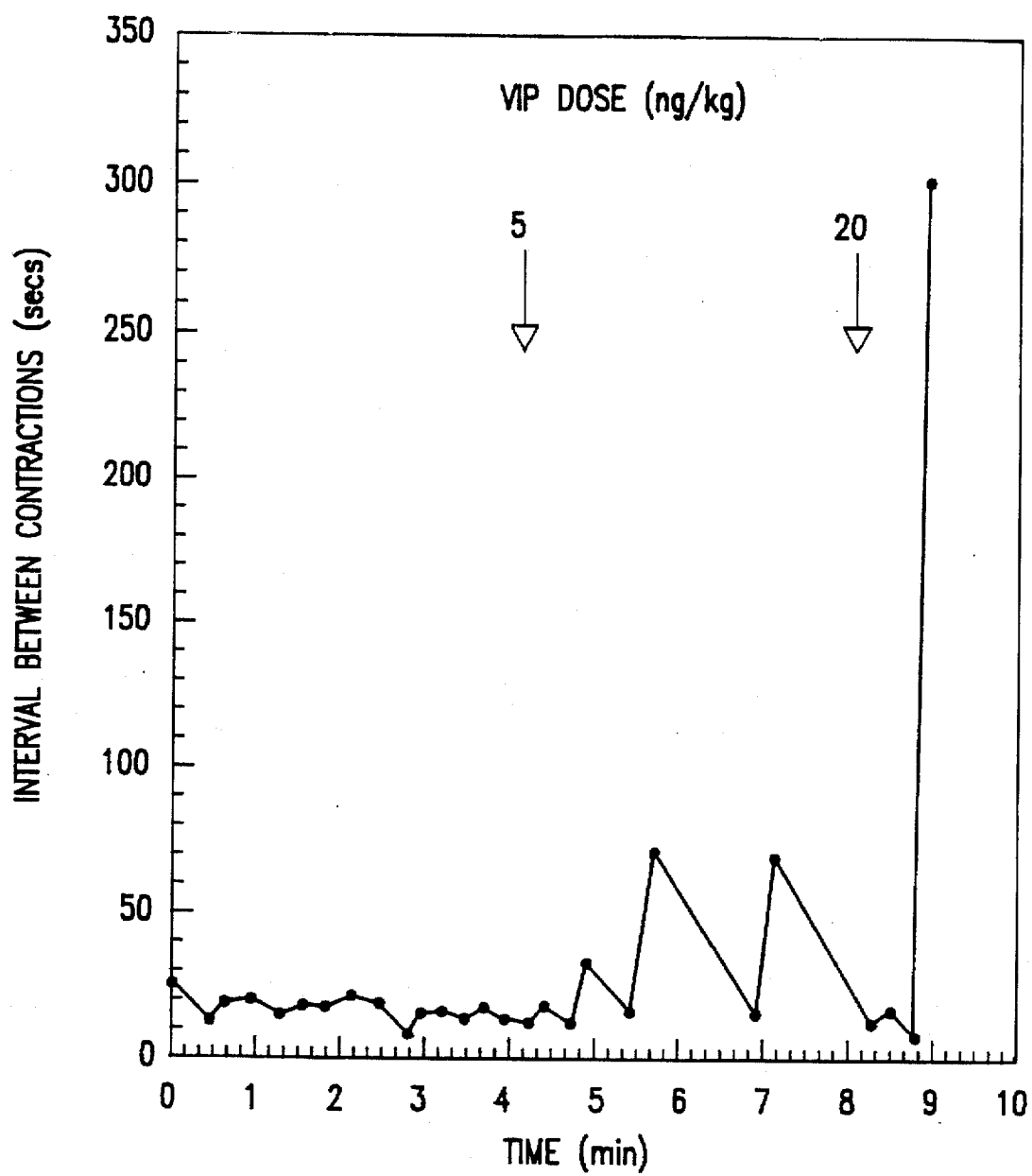
FIG. 1A, 1B, and 1C show the effect of an infusion of VIP in a patient.

In accordance with the present invention an effective dosage of VIP is administered immediately before or during an endoscopic, cystoscopic or other procedure or both, in order to induce substantial paralysis of at least the portion of interest of the gastrointestinal or urinary tract.

As used herein, the term "VIP" refers not only to the carboxyl-amidated protein whose sequence is shown in Table 1, but also to the functionally active analogues and derivatives of that protein (particularly amino terminally acetylated derivatives). A VIP analogue or derivative is said to be functionally active when, upon administration to a patient, it is capable of producing a short-lived paralysis of at least a portion of the gastrointestinal tract. Such analogues and derivatives include VIP species which contain or lack one, two, three, or more amino acids from either the amino or carboxyl terminus. As is known in the art, the amino acids may be present in either their protected or unprotected forms, using appropriate amino or carboxyl protecting groups. The VIP may have a free amine on its amino terminus, or it may be prepared as an acid-addition salt, or acetylated derivative. Examples of functionally active VIP analogues and functional derivatives, and methods for their preparation are disclosed in U.S. Pat. Nos. 4,605,641 (Bolin et al.); 4,734,400 (Bolin et al.); 4,822,774 (Ito et al.); 4,835,252 (Musso et al.); 4,939,224 (Musso et al.); 5,055,302 (Laties et al.), all herein incorporated by reference). The present invention is illustrated below using the preferred VIP compound depicted in Table 1.

Before being administered, the VIP is normally admixed with sterile water and saline or other pharmaceutically acceptable carrier to a concentration in the range of between about 1 µg/ml and 100 µg/ml and preferably between about 5 µg/ml and 25 µg/ml. The VIP solution may be administered by either intravenous infusion, or belus (preferably intramuscular) injection. Usually, an injection is given in the arm.

Use of a fiberoptic or video endoscope enables gastric, intestinal, or colonic motility to be visualized. In an endoscopic or cystoscopic procedure, the VIP is preferably administered during the course of the procedure after the endoscope or cystoscope has been inserted. In this manner, the frequency of. contractions can be ascertained and the dose of VIP adjusted accordingly. The effect of the VIP in reducing gastrointestinal motility is almost immediate upon being administered to a patient.

There is a wide variability in patient sensitivity to VIP. Therapeutically effective dosages can range from about 0.05 µg to 1 µg VIP per kilogram of body weight. In particular patients even higher dosages may be required to achieve substantially complete cessation of motility. In any case, the required dosages of VIP are at least an order of magnitude lower than presently used dosages of glucagon, and there is a much wider margin of safety as far as over-dosages are concerned. Ultimately, the physician has discretion in determining the therapeutically effective amount of VIP to be used in the practice of the present invention.

A further advantage of the use of VIP during endoscopic procedures is that it is effective to dilate blood vessels, thereby facilitating procedures such as examination, and treatment of venous and arteriovenous anomalies. Thus, injection of VIP into an arteriovenous malformation (AVM). itself, both enhances the AVM and relieves contractions associated with it. The physician is then better able to treat the AVM.

The patient is preferably first sedated with a narcotic such as meperidine used alone or in conjunction with a benzodiazepine such as midazolam. The endoscope or cystoscope is then introduced into the esophagus, stomach, duodenum, small intestine, colon, bladder, or other area of interest depending upon the desired diagnostic determination or clinical procedure. There is a brief period where vital signs are observed. VIP is then preferably administered over a short time period such as 30 seconds to one minute, through a freely flowing intravenous solution of normal saline. If additional dosages of VIP are needed during the procedure in order to attain substantial paralysis of the region of interest, or to maintain such substantial paralysis for a longer time if the initial dose begins to lose effect, such additional dosages may be administered in the same manner as described above.

The term "substantial paralysis" is intended to refer to a reduction in motility of the area of interest which is sufficient for the purposes of the procedure. If an adequate dosage of VIP is administered essentially complete paralysis of the gastrointestinal or urinary tract may normally be attained. In particular situations, however, a lesser degree of paralysis may be sufficient for the purposes of the procedure and preferred by the attending physician.

In procedures such as a barium examination of the gastrointestinal tract, the VIP may be administered in the same manner as described above; intravenous or intramuscular injection. In this case the dosage needed for substantial paralysis of the area of the interest may be determined by observing the area by fluoroscopy. In addition to eliminating active peristalsis, VIP is also effective to eliminate gastrointestinal spasms which might interfere with the examination.

The present invention also finds use as a method of dilating an intestinal blood vessel to visualize bleeding vessels or arteriovenous malformations. In this embodiment of the invention, VIP is injected into the arm or into a blood vessel during the course of an anglographic study. The VIP solution is made up beforehand by admixing VIP with sterile water and saline to a concentration in the range of 1–100 µg/ml. The blood vessel is injected with VIP while dye is injected into the anglographic catheter. Since there is variability is patient sensitivity to VIP, effective dosages will vary form patient to patient. A dosage in the range of 0.05 µg VIP per kg bodyweight to 5.0 µg VIP per kg bodyweight is usually administered. If the first dose of VIP does not produce significant dilation, the next dose of 1 µg per kg is given. This procedure can be repeated using dosages of 2 µg/kg, 5 µg/kg, and 10 µg/kg bodyweight until effective dilation is achieved.

VIP may be used in the course of vascular surgery to control arterial spasm. Occasionally during vascular surgery, arteries may go into spasm as the result of surgical manipulation. To relieve the spasm, VIP may be injected directly into the wall of the vessel or into the lumen of the vessel at a site proximal to the site of spasm. This injection may be repeated until satisfactory relaxation is achieved. Relaxation may be assessed by observing the artery relax or by demonstrating an increase in blood flow throughout the affected vessel.

The invention is further illustrated by the following specific examples which are not intended in any way to limit the scope of the invention.

EXAMPLE 1

Endoscopy Studies

Three healthy male volunteers underwent upper gastrointestinal endoscopy. Volunteers were between ages 30 and 55 and had no prior history of medical illnesses such as heart disease, pulmonary disease, or cerebrovascular disease. Patients who were on antihypertensive medications were excluded. A complete history was taken and a physical examination performed prior to the endoscopy. Upper gastrointestinal endoscopy was performed after an overnight fast and in the left lateral decubitus position. An intravenous infusion of normal saline was started, the pharynx was anesthetized with xylocaine spray and meperidine and midazolam were administered intravenously to achieve adequate sedation. A Fujinon EVE-FP endoscope was introduced into the stomach under direct vision, the stomach was insufflated with air such that the antrum was visualized and antral motility recorded on videotape.

After insertion of the endoscope there was an equilibration period of 5 minutes and then a 5–10 minute basal recording period. At the end of this period, the patient received the initial VIP infusion.

During the period of observation, vital signs (blood pressure and pulse) and symptoms were continuously recorded. The protocol was such that if the blood pressure dropped by more than 20 mm Hg systolic or diastolic or the pulse increased by more than 30 beats per minute for 2 minutes, intravenous saline was to be administered and the study terminated. In none of the three patients studied was there a need to terminate the study.

Sterile lyophilized VIP provided by Bachem Inc. was diluted initially in sterile water to a concentration of 100 micrograms in 1 ml. Ten minutes prior to the endoscopic procedure, the VIP solution was diluted with sterile saline to its final concentrations of 10 µg and 1 µg per ml. An initial dose of the VIP solution in the amount of 5 ng per kilogram bodyweight was administered over a 30 second period through a freely flowing intravenous solution of normal saline. For the three patients in this study, the first dose administered was 5 ng VIP per kilogram bodyweight using the 1 µg per ml solution. If gastrointestinal motility was not completely abolished, a second dose of 20 ng per kg bodyweight was given using the 10 µg per ml solution. Subsequent increasing dosages of 100 ng/kg and 300 ng/kg bodyweight were administered if antral contractions were not completely abolished at the preceding lower dosage.

During the basal observation period and the administration of the VIP solution, gastric motility was recorded continuously on ¾ inch, time stamped videotape. The minimum time-stamp interval was 1 second. Assessment of peristalsis was made by observing in real-time the presence of antral contraction waves. The protocol was such that if contractions were abolished by the first dose of VIP administered, the study was considered completed. The patient was then continually monitored until normal peristaltic contractions returned. If there was no significant diminution of antral contraction, the next dose of VIP was given. Thirty seconds after administration of the next dose of VIP, assessment of peristalsis was made again and if the administered dose abolished contractions, the study was considered completed. If the administered dose did not abolish contractions, the next highest dose was administered. This protocol was repeated as necessary until the appropriate dose to eliminate contraction was established for the particular patient.

Videotapes of the three patients studied were reviewed and the number of contractions per minute, the interval between contractions, and the force of contractions determined. Force of contraction was measured on a scale of 0 through 5, with the absence of contraction ranked as 0 and a lumen occluding contraction ranked as 5.

Figure 1B:
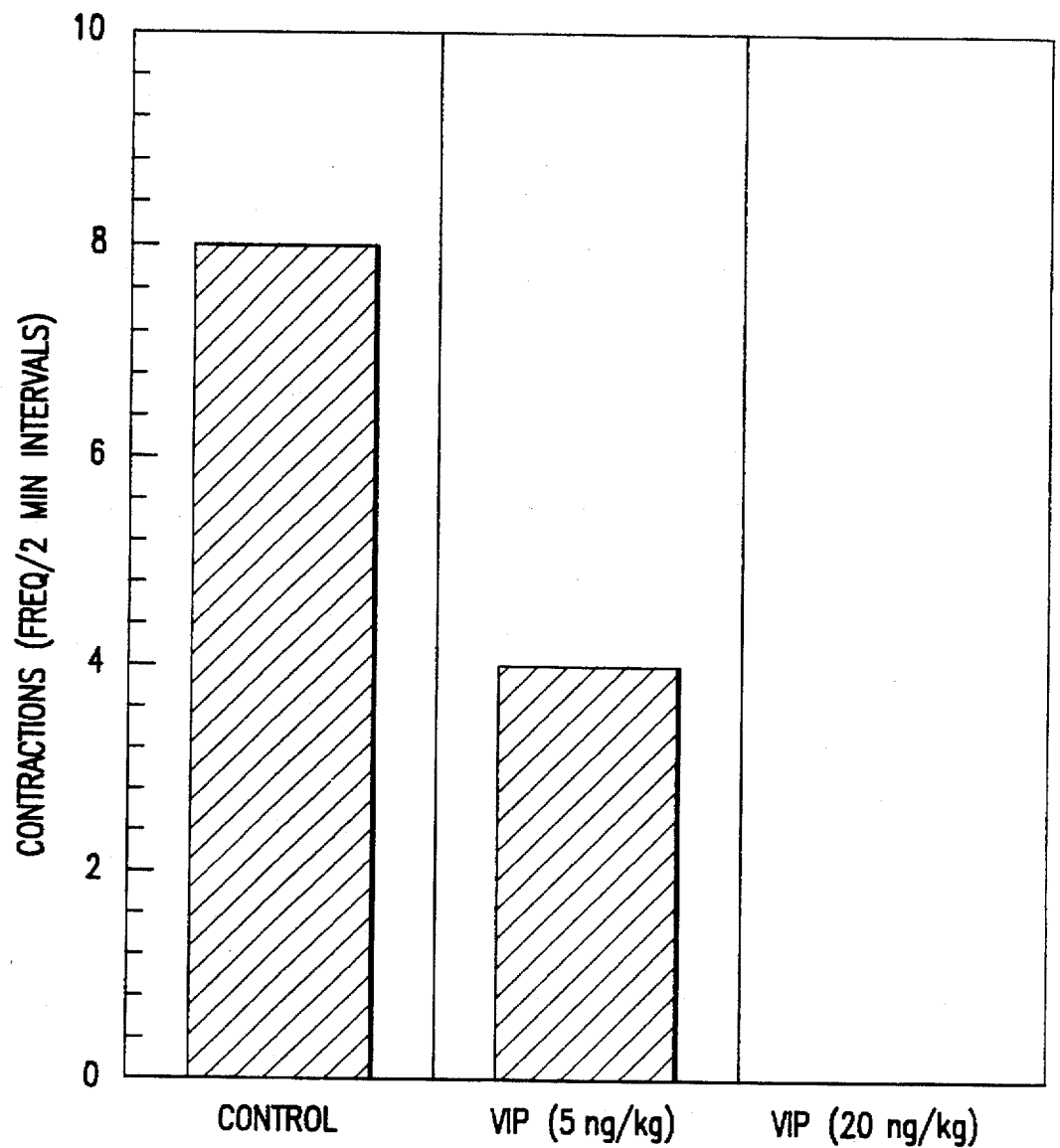
Figure 1C:
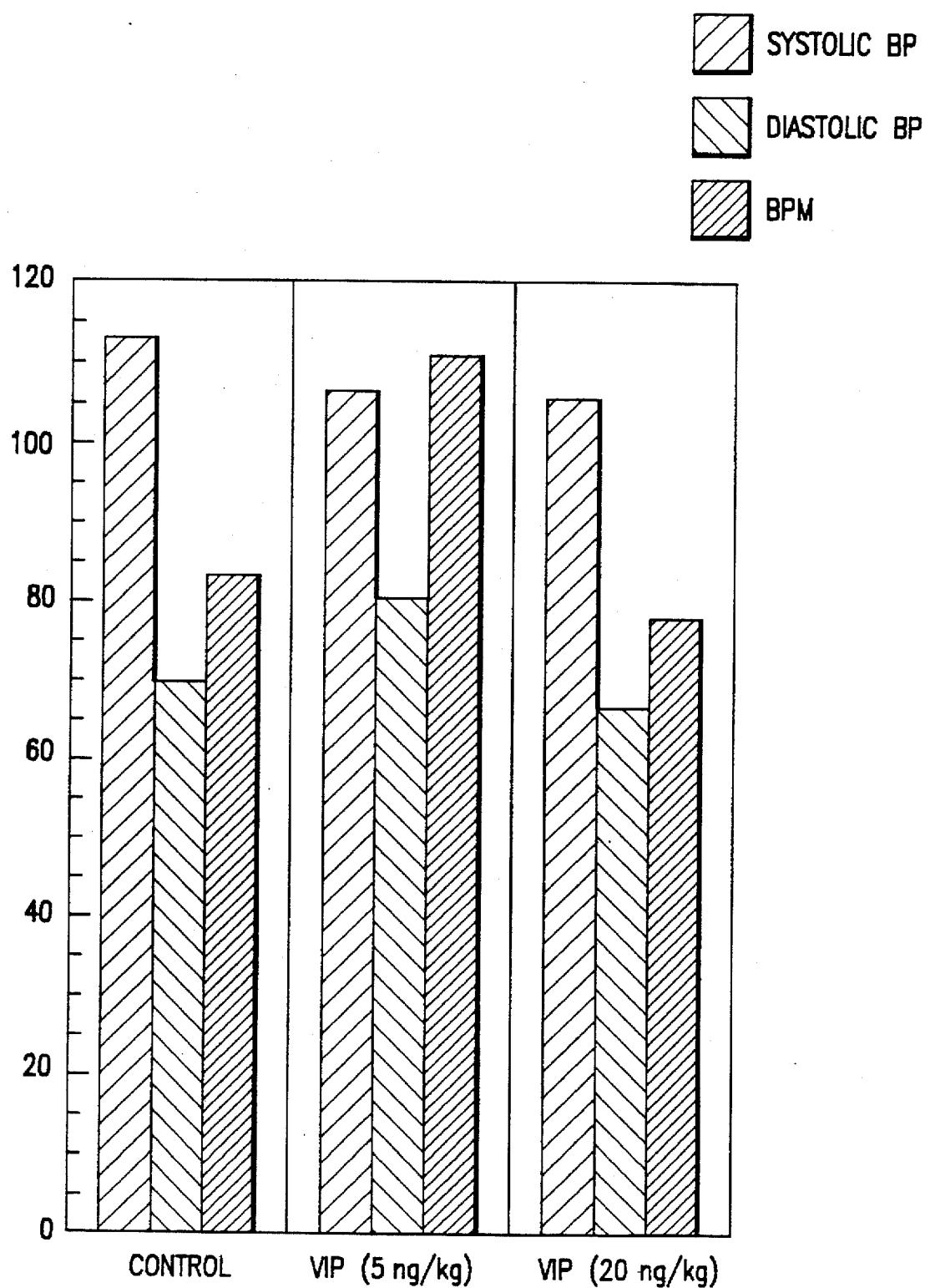

Infusion of 5 ng/kg of VIP in the first patient caused a small but significant decrease in the frequency of gastric antral contractions. See FIGS. 1A, 1B, and 1C. The number of contractions decreased in this patient from an average of 8 contractions per 2 minute interval before VIP administration to an average of 4 contractions per 2 minute interval after 5 ng VIP per kg bodyweight was injected. This decrease lasted for two minutes before contractions returned (FIGS. 1A and 1B.). Upon return of contractions, an additional dose of 20 ng VIP per kg bodyweight was administered and antral contractions were completely abolished for the remainder of the study. FIG. 1C demonstrates that in this first patient there was an initial change in blood pressure, but this did not appear to be related to the administration of VIP. The initial dose of 5 ng VIP per kg of bodyweight caused a slight decrease in systolic pressure and increase in pulse. At the higher dose level, however, these effects on blood pressure and pulse were not seen.

Figure 2A:
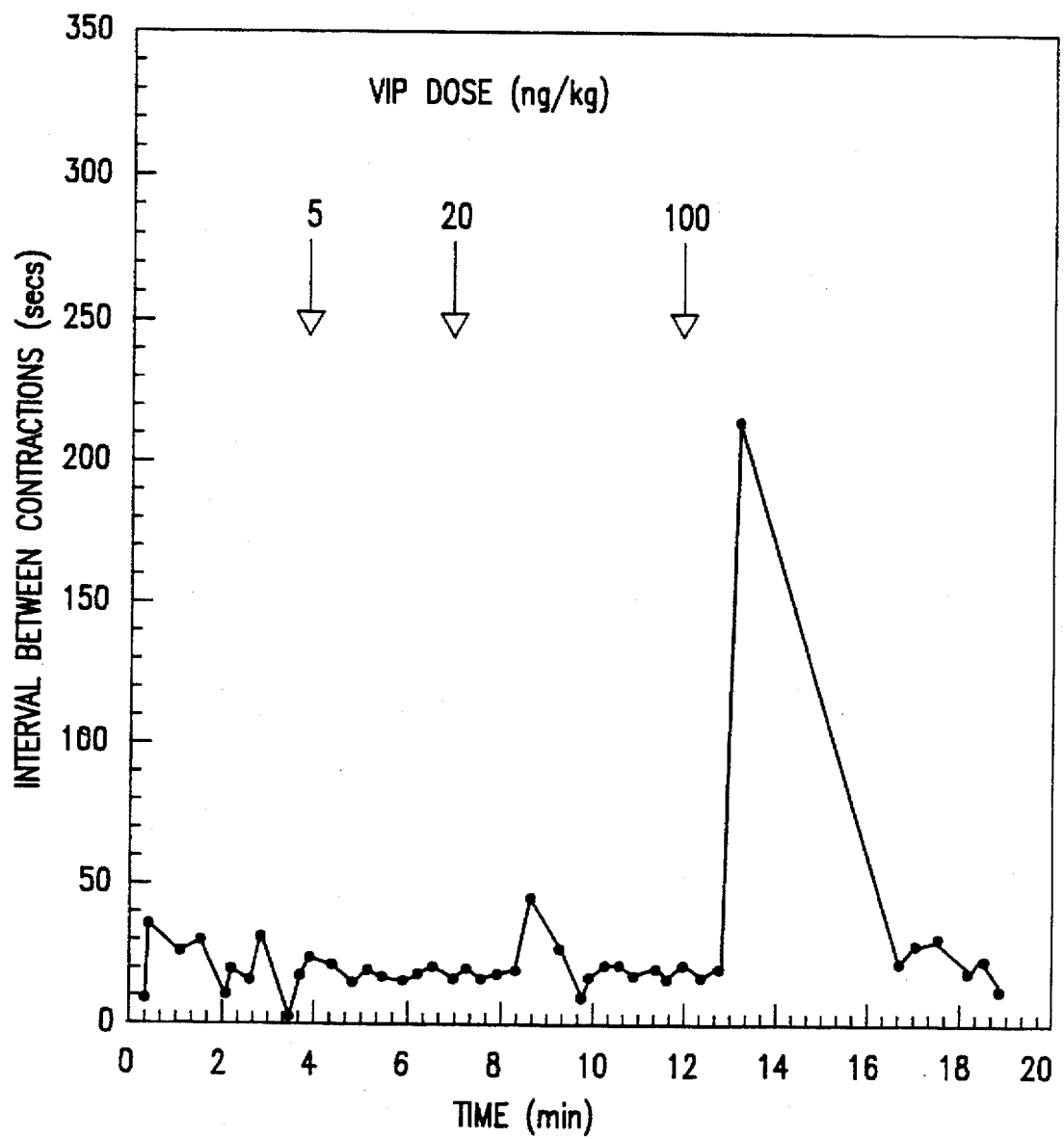
FIGS. 2A, 2B and 2C show the effect of an infusion of VIP in a second patient.
Figure 2B:
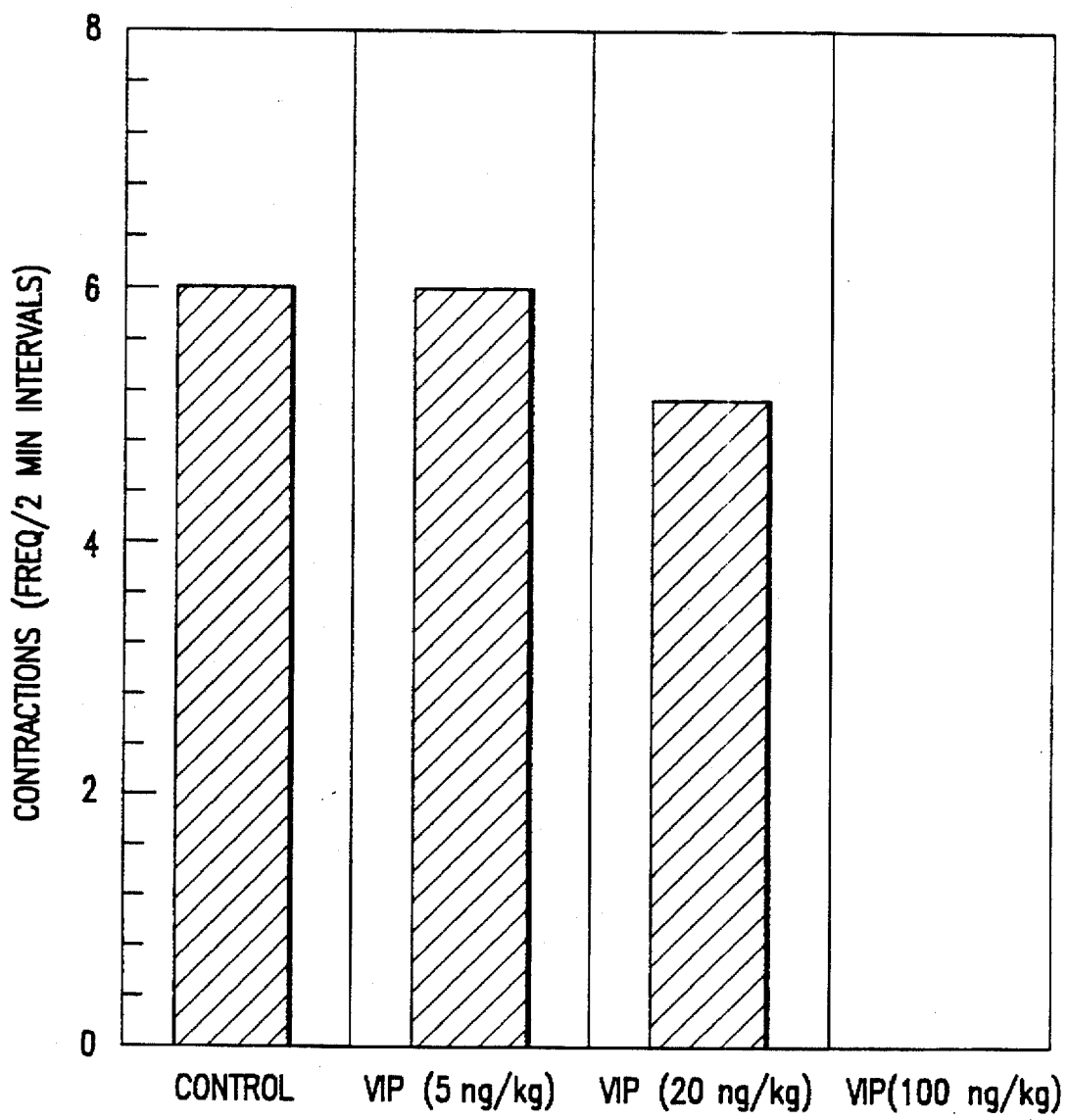
Figure 2C:
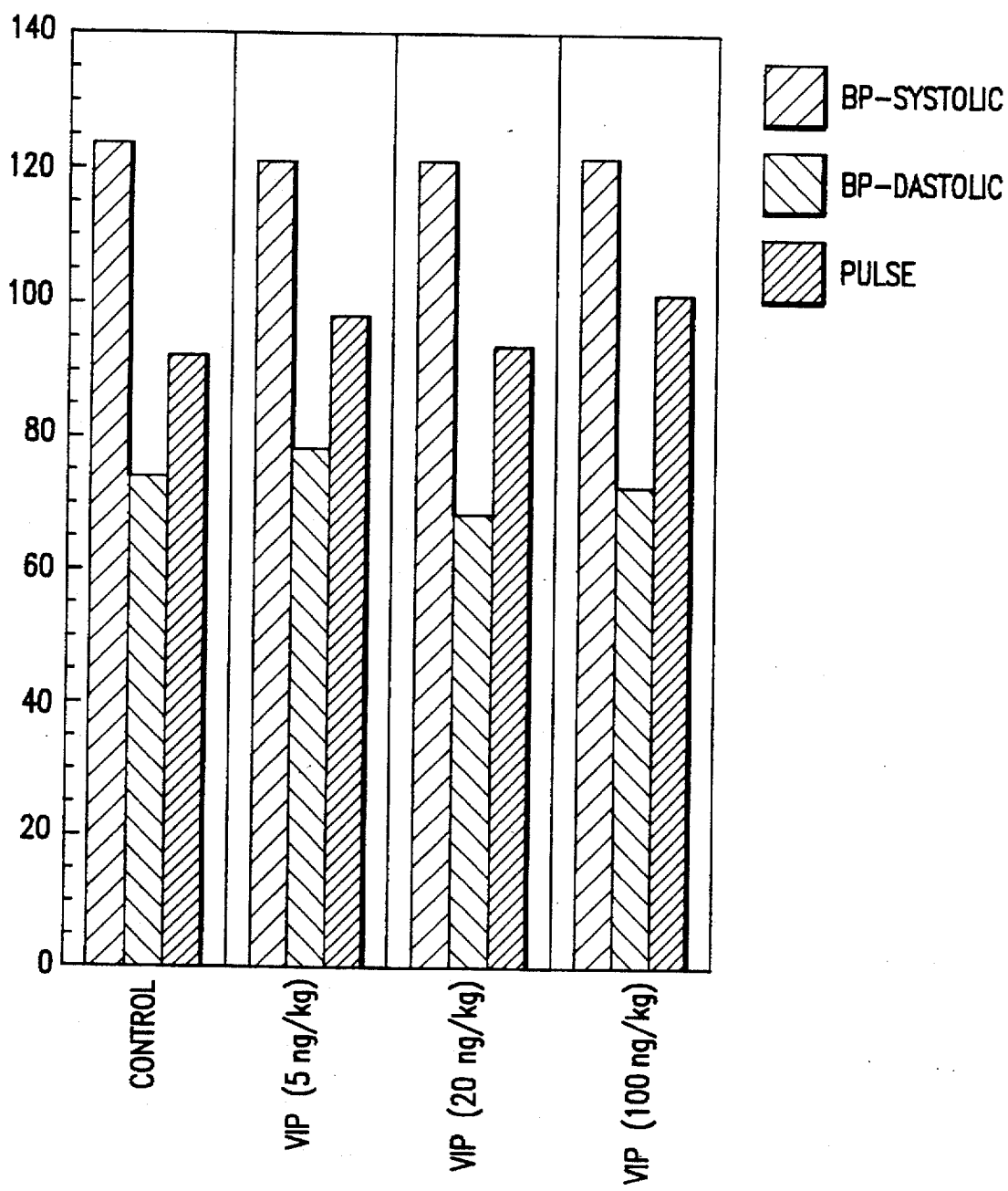

In the second patient studied, as illustrated in FIGS. 2A, 2B and 2C, VIP dosages of 5 and 20 ng/kg of bodyweight had no significant effect on gastrointestinal motility or blood pressure. The number of contractions after the first dose of 5 ng VIP per kilogram bodyweight remained at 6 contractions per 2 minute interval. A dose of 20 ng VIP/kg barely affected the number of contractions occurring. However, VIP infusion of 100 ng/kg resulted in a significant reduction in gastrointestinal motility. There was no significant change in blood pressure or pulse at any of the dosages tested in this particular patient.

Figure 3A:
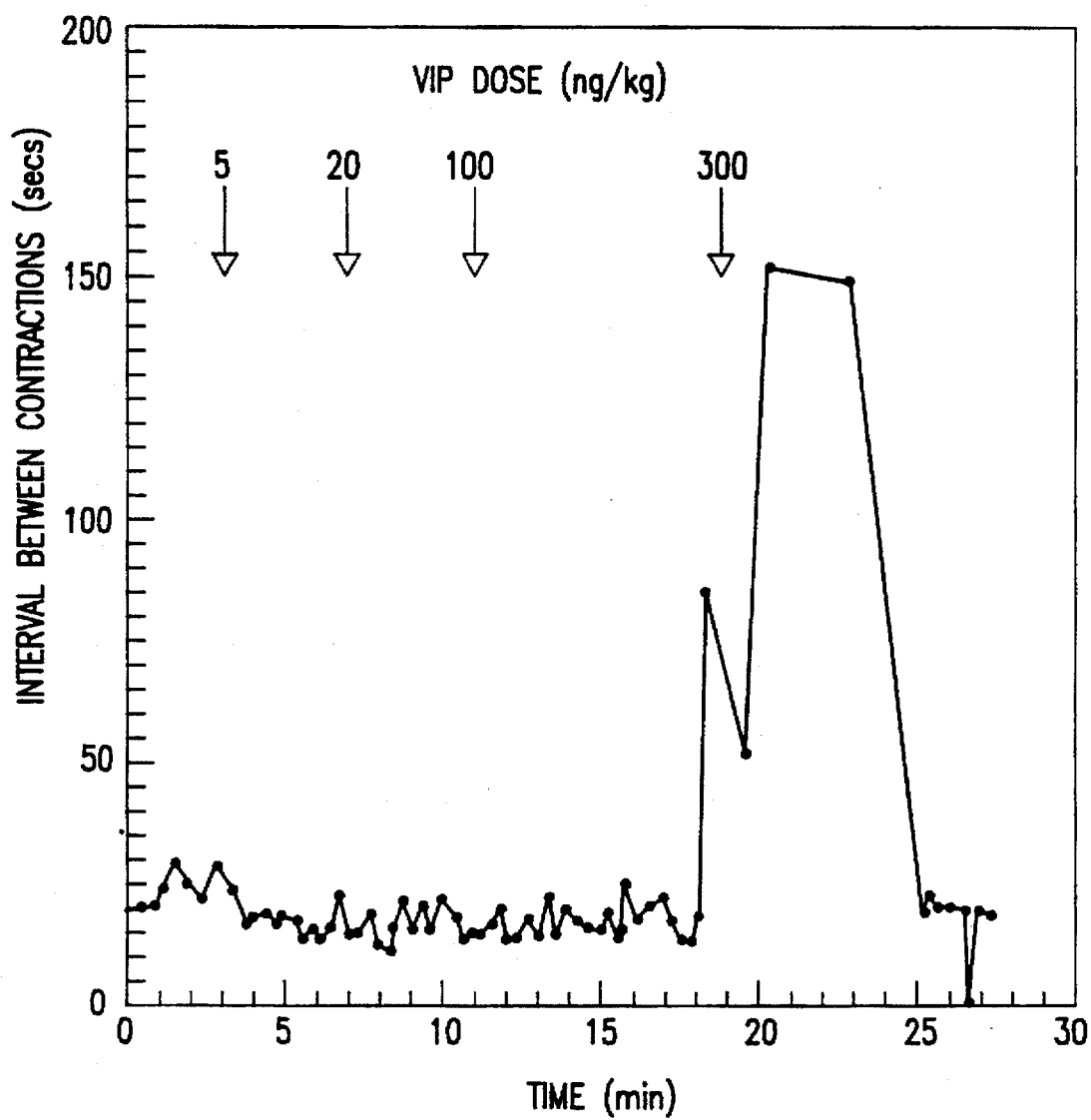
FIGS. 3A, 3B and 3C illustrate results of an infusion of VIP obtained in a third patient for those parameters measured.
Figure 3B:
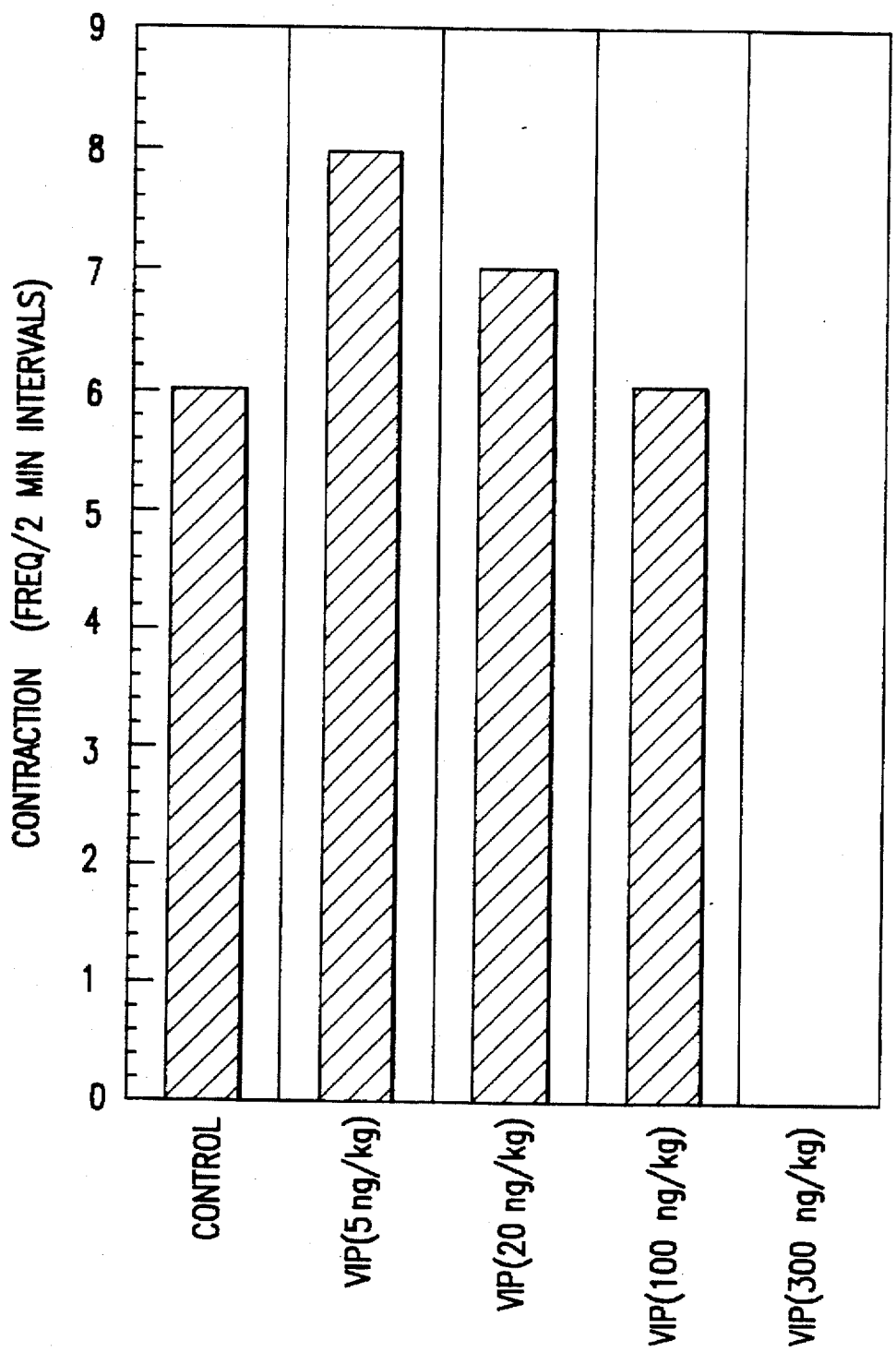
Figure 3C:
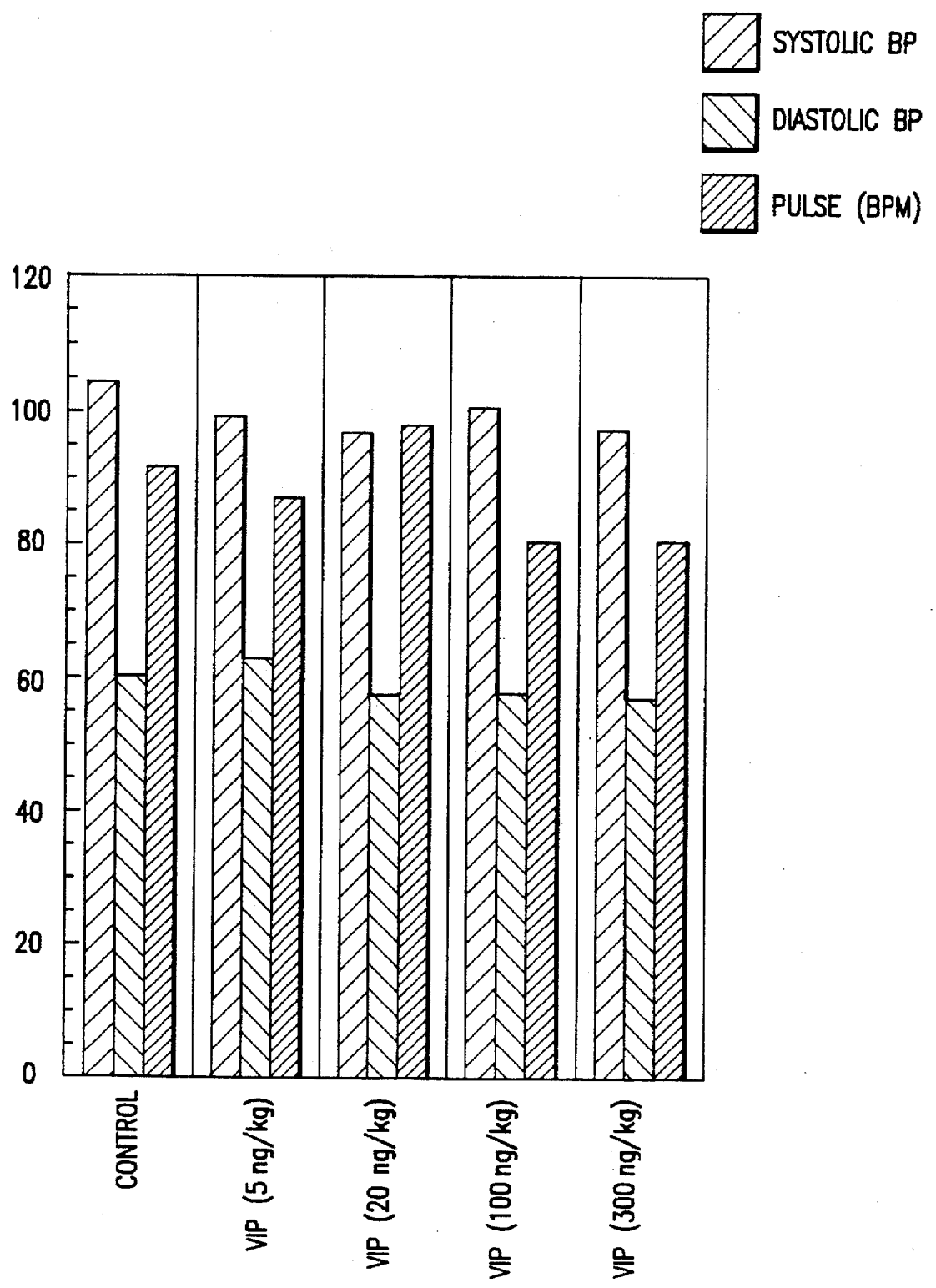

FIGS. 3A, 3B and 3C illustrate results obtained in the third patient for those parameters measured. VIP infusions of 0.05, 0.02 and 0.1 µg/kg has no effect on antral motility. VIP at a dose of 0.3 µg/kg, however, resulted in a decrease in motility for seven minutes. In addition, there was no significant change in blood pressure or pulse with any dose of VIP administered to this particular patient.

None of the three patients studied experienced any adverse reactions to VIP such as nausea or vomiting.

EXAMPLE 2

Cystoscopy Studies

The patient is first sedated with a narcotic such as meperidine used alone or in conjunction with a benzodiazepine such as midazolam. The cystoscope is then introduced into the bladder. There is a brief period where vital signs are observed. The VIP is then administered over a 30 second period through a freely flowing intravenous solution of normal saline. An initial dose of 5 ng VIP per kg bodyweight is administered. If the contractions are not reduced significantly, the next higher dose of 20 ng/kilogram bodyweight is administered. If contractions are not abolished at this dose, increasing dosages of 100 and 300 ng VIP per kilogram bodyweight or higher are administered, while monitoring the patient's blood pressure and pulse until contractions are eliminated.

EXAMPLE 3

Barium Examination

When used for inducing a temporary paralysis of the gastrointestinal tract during a barium exam, VIP is admixed with sterile water and saline to a concentration in the range of 1–100 µg/ml, and then administered immediately prior to or during the barium exam by either intramuscular injection or intravenous infusion.

Preferably the VIP is administered during the barium exam. The patient will be lying on the examination table after a barium meal or enema. While under the fluoroscope, the attending physician is able to visualize any area of the gastrointestinal tract where contractions or spasms maybe occurring and obscuring the physician's visibility. If the physician observes spasms occurring, VIP is administered by infusion over a 30 second period through a freely flowing intravenous solution of normal saline. The injection is usually given in the arm. An initial dose of 0.05 μg VIP per kg bodyweight is administered. If the spasms or contractions are not eliminated, the next higher dose of 1 μg VIP per kilogram bodyweight is administered. If spasms or contractions are still not eliminated, increasing dosages are given, starting at 2 μg VIP per kilogram bodyweight and going as high as 5 μg VIP per-kilogram bodyweight or higher until spasms or contractions are abolished.

EXAMPLE 4

Use in Myocardial Imaging

Myocardial imaging techniques are important methods for the diagnosis and treatment of disorders of the heart (Ellis, S. G. et al., *J. Amer Coll. Cardiol.* 19:681–686 (1992); Brook, R. H. et al., *New. Eng. J. Medicine* 323:1173–1177 (1990); Rao, P. S., *Clin. Cardiol.* 12:618–628 (1989)). Several of the techniques are used to identify areas of the myocardial tissue that are ischemic: that is, have reduced blood flow. The reduced blood flow is usually due to atherosclerosis of the coronary arteries supplying specific areas of heart muscle (see, Manyari, D. E. et al., *Clin. Invest. Med.* 2:76–93 (1986)). When blood flow to areas of the myocardium is unable to supply adequate oxygen for normal function, the muscle becomes ischemic or infarcted. Ischamia is reversible injury. The myocardial tissue remains viable but is at risk for cell death (myocardial infarction) if flow is inadequate for an excessive period of time.

Thallium scintigraphy is a technique where a radioactive chemical is injected into the body and taken up by healthy myocardial tissue (Kottler, T. S. et al., *Ann. Intern. Med.* 113:684–702 (1990); Iskandrian, A. S., *Amer. Heart J.* 122:279–284 (1991); see also, Bjorkhem, G. et al., *Pediatr. Cardiol.* 11:1–7 (1990)). The areas of uptake are detected by sensitive external detectors. Infarcted and ischemic myocardial tissue does not take up thallium and appears as a "cold" spot on the study. Exercise may produce ischemia in myocardium at risk when the blood flow is less than the demand for oxygen. Under these conditions thallium uptake is decreased with exercise and a "cold spot" appears. This "cold spot" fills in with rest as compared to infarcted areas where the defect remains. Adenosine and dipyridimole have been proposed as agents that can be injected by vein and may improve the sensitivity of detecting areas of ischemia by enhancing the appearance of reversible "cold spots."

VIP may be used to enhance the sensitivity of thallium scintigraphy and other myocardial imaging techniques. VIP dilates normal coronary vessels but may not dilate atherosclerotic vessels. Thus, at rest and during exercise VIP infusion would "steal" blood from the diseased vessels by reducing the resistance to flow in normal vessels. This "steal" phenomenon would increase the likelihood of the appearance of a "cold spot" in ischemic myocardium at levels of lower exercise and possibly without exercise. VIP at 0.3 to 1.0 μg/kg would be given as an injection over 30 secs or as a continuous infusion during the test. Because the effect of the drug is transient and side effects are few this approach represents a safe alternative to other agents that are used to enhance thallium imaging.

I claim:

1. A method of inducing a temporary substantial paralysis of a portion of interest of the gastrointestinal tract in a patient during endoscopy or other medical procedure comprising:

administering to the patient an initial dosage of VIP prior to or during said procedure; and optionally administering, one or more additional dosages of VIP until the frequency and severity of contractions no longer interfere with such procedure.

2. A method according to claim 1 further comprising: monitoring the effect of such initial dosages on reducing or eliminating contractions.

3. A method of inducing a temporary substantial paralysis of a portion of interest of the gastrointestinal tract in a patient during endoscopy or other medical procedure, said method comprising:

administering to the patient an initial dosage of VIP prior to or during said procedure; and optionally, administering one or more additional dosages of VIP until the frequency and severity of contractions no longer interfere with said procedure, wherein the total dosage administered is no more than about 10 μg/kg body weight of the patient.

4. A method according to claim 3, wherein said initial dosage is about 0.05 μg/kg of body weight or more.

5. A method according to claim 3, wherein said initial dosage is in the range of about 0.05 μg/kg body weight to 0.5 μg/kg body weight.

6. A method of inducing in a patient undergoing an endoscopic or other medical procedure, a temporary substantial paralysis of an area of interest which comprises:

administering to the patient prior to or during the course of such medical procedure a therapeutically effective amount of VIP sufficient to induce such temporary substantial paralysis, said VIP being admixed with a physiologically acceptable carrier.

7. A method according to claim 6 wherein the therapeutically effective amount of VIP is between 0.05 and 10 μg per kilogram of bodyweight of such patient.

8. A method according to claim 3 wherein said initial dosage is administered before the start of said procedure and said one or more additional dosages are administered throughout the course of said procedure as needed to maintain said substantial paralysis.

9. A method according to claim 3 wherein said initial dosage is administered before said procedure by bolus injection, and said one or more additional dosages are administered throughout the course of said procedure by intravenous infusion.

10. A method according to claims 8 or 9 wherein said procedure is an endoscopy.

11. A method according to claims 1 or 3 wherein said portion of interest is the esophagus.

12. A method for enhancing visualization of an area of interest in the gastrointestinal tract in a patient during a barium examination, said method comprising administering VIP to said patient in an amount sufficient to relieve spasms in said area of interest, whereby visualization of said area is enhanced.

13. A method for enhancing visualization of an intestinal blood vessel during angiographic study, said method comprising:

administering VIP to said patient in an amount sufficient to dilate said blood vessel, whereby visualization of said blood vessel is enhanced.

14. A method of inducing a temporary substantial paralysis of a portion of interest of the gastrointestinal tract of a patient during endoscopy or other medical procedure, said method comprising:

administering to the patient an initial dosage of VIP of about 0.05 µg/kg of body weight or more prior to or during said procedure; and optionally, administering one or more additional dosages of VIP until the frequency and severity of contractions no longer interfere with such procedure.

15. A method of inducing a temporary substantial paralysis of a portion of interest of the gastrointestinal tract in a patient during endoscopy or other medical procedure comprising:

administering to the patient an initial dosage of VIP in the range of 0.05 µg/kg body weight to 0.5 µg/kg body weight prior to or during said procedure; and, optionally administering one or more additional dosages of VIP until the frequency and severity of contractions no longer interfere with such procedure.

16. The method according to claims 1, 3 or 12 in which said VIP is administered by intravenous infusion.

17. The method according to claims 1, 3 or 12 in which said VIP is administered by intramuscular injection.

18. The method according to claims 1, 3 or 12 further comprising administering to a patient said VIP in combination with a benzodiazepine and a narcotic analgesic selected from the group consisting of meperidine, fentanyl, diazepam and midazolam and mixtures thereof.

19. The method according to claims 6 or 12 wherein said area of interest is the esophagus.

* * * * *